United States Patent [19]

Merger et al.

[11]  4,282,368

[45]  Aug. 4, 1981

[54] PREPARATION OF P-SUBSTITUTED AROMATIC CARBAMIC ACID ESTERS

[75] Inventors: Franz Merger, Frankenthal; Gerhard Nestler, Ludwigshafen, both of Fed. Rep. of Germany

[73] Assignee: BASF Aktiengesellschaft, Fed. Rep. of Germany

[21] Appl. No.: 155,762

[22] Filed: Jun. 2, 1980

[30] Foreign Application Priority Data

Jun. 23, 1979 [DE] Fed. Rep. of Germany ....... 2925480

[51] Int. Cl.$^3$ ................ C07C 125/065; C07C 125/067
[52] U.S. Cl. ....................................... 560/24; 560/27; 560/28; 560/30; 560/31; 560/32
[58] Field of Search ....................... 560/24, 27, 28, 30, 560/31, 32

[56] References Cited

U.S. PATENT DOCUMENTS 2,860,166  11/1958  Newcomer et al. ................... 560/24

FOREIGN PATENT DOCUMENTS 183416  10/1955  Austria .

OTHER PUBLICATIONS

Müller, Houben–Weyl, Methoden der Organischen Chemie, vol. 11/1, pp. 137–145 and 948 (1971).
Foerst, Ullmanns Encyklopädie der technischen Chemie, vol. 5, pp. 73–76 (1954).
Donnley et al., Chem. Absts., 51, 16325(f), (1957).

*Primary Examiner*—G. T. Breitenstein
*Attorney, Agent, or Firm*—Keil & Witherspoon

[57] ABSTRACT p-Substituted, aromatic carbamic acid esters are prepared by reacting an aromatic carbamic acid ester with an olefin in the presence of an inorganic acid or sulfonic acid.

The aromatic carbamic acid esters obtainable by the process of the invention are active ingredients for pesticides and drugs, as well as valuable starting materials for the preparation of such ingredients and of dyes.

12 Claims, No Drawings

PREPARATION OF P-SUBSTITUTED AROMATIC CARBAMIC ACID ESTERS

The present invention relates to a novel process for the preparation of p-substituted aromatic carbamic acid esters by reacting an aromatic carbamic acid ester with an olefin in the presence of an inorganic acid or a sulfonic acid.

Houben-Weyl, Methoden der Organischen Chemie, volume 11/1, pages 137–145, discloses the preparation of aromatic carbamic acid esters by reacting the corresponding aromatic amine with a chloroformic acid ester in the presence of an acid acceptor, or by reacting the corresponding aryl isocyanate with an alcohol. The essential disadvantage of these processes is that they start from anilines with a para-alkyl substituent in the nucleus, and it is known that such anilines can only be prepared with difficulty. All the above processes are unsatisfactory in respect of yield and of simplicity and economy of operation.

We have found that a p-substituted, aromatic carbamic acid ester of the formula

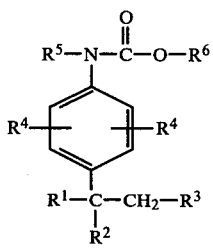

where the individual radicals $R^1$, $R^2$, $R^3$, $R^4$, $R^5$ and $R^6$ may be identical or different and each is an aliphatic radical, $R^1$, $R^2$ and $R^3$ may also each be a cycloaliphatic, araliphatic or aromatic radical, any 2 of the radicals $R^1$, $R^2$ and $R^3$ may also, conjointly with the adjacent carbon atoms, be members of an alicyclic ring, $R^1$, $R^2$ and $R^3$ conjointly with the adjacent carbon atoms may also be a bicyclic radical, $R^2$, $R^3$ and $R^5$ may also each be hydrogen, $R^4$ may also be hydrogen or halogen and $R^6$ may also be a cycloaliphatic radical, is obtained in an advantageous manner if an aromatic carbamic acid ester of the formula

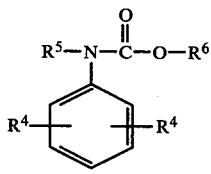

where $R^4$, $R^5$ and $R^6$ have the above meanings, is reacted with an olefin of the formula

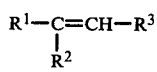

where $R^1$, $R^2$ and $R^3$ have the above meanings, in the presence of an inorganic acid or sulfonic acid.

Where ethyl N-phenylcarbamate and isobutene are used, the reaction may be represented by the following equation:

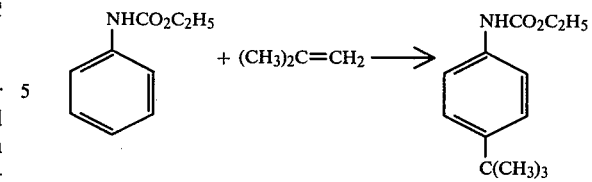

Compared to the conventional methods, the process according to the invention surprisingly gives a large number of p-substituted aromatic carbamic acid esters more simply and more economically, and with better space-time yield and higher purity, particularly on an industrial scale and in continuous operation. It was surprising that the p-substitution reaction of an N-arylcarbamic acid ester can be carried out with good yield using only a catalytic amount of an acid. In view of the disclosure that carbamic acid esters are cleaved in the presence of acids (Houben-Weyl, volume 11/1, page 948), it was furthermore not to be expected that the substitution in the presence of acids is feasible without the formation of heterogeneous mixtures containing substantial amounts of by-products.

The olefin III can be reacted with the aromatic carbamic acid ester II in stoichiometric amount or in greater or lesser amount than this; preferably, from 0.3 to 5, especially from 0.5 to 4, moles of olefin are used per mole of carbamic acid ester II. Preferred aromatic carbamic acid esters II and olefins III and, accordingly, preferred aromatic carbamic acids I are those where the individual radicals $R^1$, $R^2$, $R^3$, $R^4$, $R^5$ and $R^6$ may be identical or different and each is alkyl of 1 to 10, especially 1 to 4, carbon atoms, $R^1$, $R^2$ and $R^3$ may also each be cycloalkyl of 5 to 8 carbon atoms, aralkyl or alkylaryl of 7 to 12 carbon atoms or phenyl, any 2 of the radicals $R^1$, $R^2$ and $R^3$ may also, conjointly with the adjacent carbon atoms, be members of an alicyclic ring of 5 to 8 carbon atoms, $R^1$, $R^2$ and $R^3$ conjointly with the adjacent carbon atoms in the starting material III may also be norbornene and in that case correspondingly are a norbornyl radical in the end product I, $R^2$, $R^3$ and $R^5$ may also each be hydrogen, $R^4$ may also be hydrogen, bromine or chlorine, and $R^6$ may also be cycloalkyl of 5 to 8 carbon atoms. The above radicals and rings may in addition be substituted by groups which are inert under the reaction conditions, for example alkyl or alkoxy of 1 to 5 carbon atoms, or chlorine or bromine present as substituents of the phenyl radical.

The use of branched alkenes is preferred. In contrast to the conventional processes, it can also be advantageous to use mixtures of alkenes, or of alkenes with alkanes, such as are produced, for example, by cracking or dehydrogenation of hydrocarbons, eg. petroleum, or by oligomerization of olefins, especially of isobutylene, propylene or n-butene, or by hydrogenation of carbon monoxide. Instead of the olefins, compounds which form olefins under the reaction conditions, for example ethers, eg. methyl tert.-butyl ether, esters, eg. tert.-butyl acetate, or alcohols, eg. tert.-amyl alcohol or tert.-butanol, may also be employed.

Examples of olefins which may be used as starting materials III include the following: n-pent-1-ene, n-hex-1-ene, n-hept-1-ene, n-oct-1-ene, n-non-1-ene, n-dec-1-ene, n-undec-1-ene, n-dodec-1-ene, prop-1-ene and n-but-1-ene; the above alkenes substituted in the 2- or 3- or 4-position by methyl, ethyl, n-propyl, isopropyl, n-butyl, isobutyl, sec.-butyl or tert.-butyl; 2,3-dimethyln-butene, 3,3-dimethyl-n-butene, 2-methyl-3-ethylpentene, 3-methyl-3-ethylpentene, 2,3,3-trimethylheptene, 2,4,4-trimethylpentene, 2,3,3-trimethylpentene and 2,3,4-trimethylpentene; corresponding alkenes with the double bond in the 2-position or 3-position of the molecule; branched alkenes, such as those obtained as mixtures on dimerizing isobutylene or n-butene (octenes) or trimerizing isobutylene or n-butene (dodecenes) or propylene (nonenes) or tetramerizing propylene (dodecenes); O-methylstyrene, m-methylstyrene, p-methylstyrene, 3,5-dimethylstyrene, o-ethylstyrene, m-ethylstyrene, p-ethylstyrene and 4-chlorostyrene; cycloheptene, α-methylstyrene, norbornene, cyclohexene and 1-methylcyclohexene.

The following are preferred: propylene, isobutylene, styrene, n-octenes, n-nonenes, n-decenes and n-dodecenes, 2,3-dimethylbut-1-ene, 2-methylbut-1-ene, 2-methylbut-2-ene, n-butene, 2-ethylbut-1-ene, cyclopentene, cyclohexene, α-methylstyrene and norbornene.

Examples of suitable aromatic carbamic acid esters II are methyl phenylcarbamate which is unsubstituted, or monosubstituted in the 2-, 3-, 5- or 6- position, or disubstituted (the substituents being identical or different) in the 2,3-, 2,5- or 2,6- position by chlorine, bromine, methyl, ethyl, propyl, isopropyl, butyl or isobutyl; the corresponding methyl N-methyl-, N-propyl-, N-ethyl-, N-isopropyl-, N-butyl- and N-isobutyl-phenylcarbamates; and homologous ethyl, propyl, isopropyl, butyl, isobutyl, cyclohexyl, cyclopentyl, cycloheptyl and cyclooctyl esters; the following are preferred: methyl phenylcarbamate, o-tolylcarbamate, m-tolylcarbamate, o-chlorophenylcarbamate, m-chlorophenylcarbamate, o-ethylphenylcarbamate, o-propylphenylcarbamate, 2-chloro-6-methylphenylcarbamate, 2-chloro-5-methylphenylcarbamate, 2,6-dimethylphenylcarbamate and 2,5-dimethylphenylcarbamate, and the corresponding ethyl, propyl, butyl and cyclohexyl esters.

The reaction is in general carried out at from 25° to 160° C., preferably from 40° to 150° C., especially from 60° to 130° C., under reduced pressure, superatmospheric pressure or atmospheric pressure, preferably under a pressure of from 1 to 30 bar, more especially from 1 to 20 bar, continuously or batchwise. The residence time is preferably from 0.5 to 10 hours, especially from 0.5 to 5 hours, and the throughput is preferably from 1 to 120, especially from 5 to 50, kilograms of starting material II per kilogram of catalyst per hour. Advantageously, additional solvents are not used; however, under certain circumstances solvents which are inert under the reaction conditions may be useful, for example to lower the viscosity of the reaction mixture. Examples of suitable solvents include aliphatic and cycloaliphatic hydrocarbons, eg. heptane, nonane, gasoline fractions boiling within a range from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane; halohydrocarbons, especially chlorohydrocarbons, eg. tetrachloroethylene, 1,1,2,2-tetrachloroethane, 1,1,1,2-tetrachloroethane, dichloropropane, methylene chloride, dichlorobutane, chloroform, carbon tetrachloride, tetrachloroethane, 1,1,1-trichloroethane, 1,1,2-trichloroethane, trichloroethylene, chlorobenzene, pentachloroethane, cis-dichloroethylene, 1,2-dichloroethane and 1,1-dichloroethane; aromatic hydrocarbons, eg. benzene, toluene and xylenes; tetrahydrofuran, dioxane and methyl acetate; and mixtures of the above. Advantageously, the amount of solvent used is from 10 to 1,000 percent by weight, preferably from 50 to 200 percent by weight, based on starting material II.

The reaction is carried out in the presence of a catalyst, in the form of an inorganic acid or sulfonic acid, advantageously using from 0.01 to 0.5, especially from 0.05 to 0.3, equivalent of acid per mole of starting material II. Instead of monobasic acids, equivalent amounts of polybasic acids may also be employed. Examples of suitable acids include the following: hydrogen chloride, sulfuric acid, phosphoric acid, sulfonic acids, eg. methanesulfonic acid, benzenesulfonic acid and p-toluenesulfonic acid, fluoboric acid and mixtures of the above. The acids may be employed in a concentrated form, as mixtures with one another, or as mixtures with a solvent.

Preferred catalysts are organic cation exchangers containing sulfonic acid groups, advantageously resins consisting of styrene/divinylbenzene copolymer or other sulfonated crosslinked styrene polymers; phenol/formaldehyde and benzene/formaldehyde resins containing sulfonic acid groups; perfluorinated sulfonated polystyrene/divinylbenzene resins; perfluorinated, sulfonated crosslinked polystyrene resins; and copolymers of tetrafluoroethylene and vinylsulfonic acid. Sulfonated polystyrene/divinylbenzene exchangers are preferred. The exchangers are employed in the acid form and not as a salt. For this particular application, the catalyst advantageously has a particle size of from 5 to 2,000, preferably from 10 to 1,800, advantageously from 20 to 1,500, micrometers. It may have either a macroporous or a gel-like structure. Examples of suitable products are the exchanger resins marketed under the name LEWASORB A-10 ®, LEWATIT SPC-118 ®, AMBERLYST 15 ®, AMBERLIT IR-120 ®, DOWEX 50 ®, LEWATIT S-100 ®, NALCITE HCR ®, PERMUTIT RS ® and WOLFATIT KPS-200 ®. Advantageously, they are dehydrated, before use, in a conventional manner, for example by heating under reduced pressure at 100° C.–110° C. However, they can also be dehydrated by displacing the water with a hydrophilic organic fluid and then heating the resin at 100° C. under reduced pressure, or by azeotropic distillation with an organic fluid.

The catalyst, in the form of an ion exchanger, can be employed in any batchwise or continuous procedure, for example by using it in the form of a fixed bed. Another advantageous method is to have the ion exchanger in suspension, as a rule in the reaction mixture being formed, during the reaction. Advantageously, a proportion of the liquid carbamic acid ester II and olefin III, with or without solvent, is introduced into the reactor and the catalyst is suspended in the fluid, with thorough mixing. Advantageously, the amount of this initially introduced carbamic acid ester II or starting mixture and/or organic solvent is chosen so that the amount of catalyst, in the form of an ion exchanger, suspended in the reaction mixture being formed is from 0.3 to 30, preferably from 1 to 20, percent by weight, based on the weight of the total liquid mixture in the reaction space. Based on carbamic acid ester, the amount of ion exchanger is preferably from 1 to 70, especially from 10 to 50, percent by weight. Advantageously, the mixture is subjected to mixing during the entire reaction, preferably by stirring at not less than 100, advantageously from 200 to 2,000, especially from 300 to 1,000, revolutions per minute. Where a mixing device without a stirrer is used, including, for example, the case where mixing is effected by means of an inert gas, such as nitrogen, the mixing devices are preferably such as to introduce shearing energy corresponding to the above speed of stirring. In this way, a finely dispersed suspension is obtained.

The reaction may be carried out as follows: a mixture of starting materials II and III, and catalyst, with or without solvent, is kept at the reaction temperature for the appropriate reaction time. After removing the catalyst, the end product may be isolated in a conventional manner, for example by filtration and distillation.

Where an ion exchanger is used as the catalyst and the reaction is carried out continuously, it may be carried out in a fixed bed or, advantageously, as follows: a liquid mixture of the carbamic acid ester and olefin, with or without solvent, is passed through, and mixed with—at the reaction temperature and the reaction pressure—a suspension of catalyst in the starting mixture or in the reaction mixture and is filtered. The end product is then isolated from the reaction mixture in a conventional manner, for example by distillation. Filtration is advantageously effected before the suspension leaves the reactor. Suitable filters include acid-resistant filter cloths, wire gauze filters and sintered metal filters, provided the mesh widths or pore diameters are less than the size of the catalyst particles.

The aromatic carbamic acid esters I obtainable by the process of the invention are active ingredients and valuable starting materials for the preparation of dyes, pesticides and drugs.

The carbamic acid esters may be hydrolyzed (Houben-Weyl, volume 11/1, pages 948–952) to give the corresponding anilines, which are also important starting materials for the synthesis of active ingredients. Regarding the use of the products reference may be made to the publications mentioned earlier, to Austrian Pat. No. 183,416 and to Ullmanns Encyklopädie der technischen Chemie, volume 5, pages 73–76.

In the Examples which follow, parts are by weight and bear the same relation to parts by volume as that of the kilogram to the liter.

EXAMPLE 1

A suspension of 165 parts of ethyl N-phenylcarbamate and 50 parts of exchanger resin is prepared, in a stirred reactor, at 120° C. and a stirring speed of 300 rpm, and 100 parts of isobutene are pumped in over 2 hours. This introduction of isobutene brings the pressure to 2 bar. The exchanger resin is a sulfonated styrene/divinylbenzene copolymer resin which is dehydrated for 24 hours at 100° C. under reduced pressure before being used; it has a particle size of 0.5–1.5 millimeters. After the introduction of the isobutene, the suspension in the reactor is stirred steadily at 500 rpm. After 2 hours at 120° C., the suspension is filtered and the filtrate is subjected to fractional distillation. 170 parts (77% of theory, based on ethyl N-phenylcarbamate) of ethyl N-(4-tert.-butylphenyl)-carbamate are obtained; boiling point 125° C.–127° C./0.2 mbar. The conversion is 80 percent (based on carbamic acid ester II).

EXAMPLE 2

A suspension of 165 parts of ethyl N-phenylcarbamate and 30 parts of exchanger resin is prepared in a stirred reactor at 100° C., at a speed of stirring of 300 rpm, and 130 parts of styrene are introduced, under 1 bar pressure, over one hour. The exchanger resin is a sulfonated styrene/divinylbenzene copolymer resin which before use is dehydrated for 24 hours at 100° C. under reduced pressure; it has a gel structure and a particle size of 20–150 micrometers. After the addition of the styrene, the suspension in the reactor is stirred for one hour at 100° C. at 300 rpm. The catalyst is then separated off, unconverted starting material is distilled off under reduced pressure and the residue is recrystallized from cyclohexane. 240 parts (89% of theory, based on carbamic acid ester) of ethyl N-(4-(α-methylbenzyl)-phenyl)-carbamate are obtained; melting point 78°–80° C. The conversion is 90 percent.

EXAMPLE 3

A suspension of 165 parts of ethyl N-phenyl carbamate and 50 parts of exchanger resin is prepared in a stirred reactor at 120° C., at a speed of stirring of 300 rpm, and 100 parts of 2-methylbut-2-ene are introduced, under 2 bar pressure, over one hour. The exchanger resin is a sulfonated styrene/divinylbenzene copolymer resin which before use is dehydrated for 24 hours at 100° C. under reduced pressure; it has a gel structure and a particle size of 20–150 micrometers. After the addition of the 2-methylbut-2-ene, the suspension in the reactor is stirred for 2 hours at 120° C. at 300 rpm. The catalyst is then filtered off and the filtrate distilled under reduced pressure. 195 parts (82% of theory, based on carbamic acid ester II) of ethyl N-(4-tert.-amylphenyl)-carbamate are obtained; boiling point 145°–147° C./0.3 mbar. The conversion is 84 percent (based on carbamic acid ester II).

EXAMPLE 4

A mixture of 165 parts of ethyl N-phenylcarbamate and 10 parts of 96 percent strength sulfuric acid is heated, in a stirred reactor, to 70° C. whilst stirring, and 104 parts of styrene are introduced over two hours. After completion of the addition of styrene, the mixture is stirred for a further two hours at 70° C. It is then diluted with 100 parts of toluene, neutralized with aqueous sodium carbonate solution and distilled under reduced pressure.

After recrystallization from cyclohexane, 185 parts (69% of theory, based on carbamic acid ester II) of ethyl N-(4-(α-methylbenzyl)-phenyl)-carbamate are obtained; melting point 78°–80° C. The conversion is 75 percent.

EXAMPLE 5

A mixture of 165 parts of ethyl N-phenylcarbamate and 10 grams of p-toluenesulfonic acid is heated, in a stirred autoclave, to 100° C. whilst stirring, and 112 parts of isobutene are pumped in over two hours. After completion of the addition of isobutene, the mixture is stirred for a further two hours at 100° C. It is then diluted with 100 parts of toluene and extracted with aqueous sodium carbonate solution, and the end product is distilled under reduced pressure. 169 parts (72% of theory, based on carbamic acid ester II) of ethyl N-(4-tert.-butylphenyl)-carbamate, of boiling point 125°–127° C./0.2 mbar, are obtained. The conversion is 76 percent.

We claim:

1. A process for the preparation of a p-substituted, aromatic carbamic acid ester of the formula

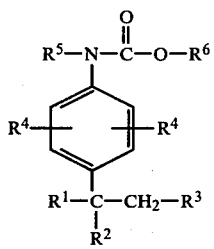

where the individual radicals $R^1$, $R^2$, $R^3$, $R^4$, $R^5$ and $R^6$ may be identical or different and each is an aliphatic radical, $R^1$, $R^2$ and $R^3$ may also each be a cycloaliphatic, araliphatic or aromatic radical, any 2 of the radicals $R^1$, $R^2$ and $R^3$ may also, conjointly with the adjacent carbon atoms, be members of an alicyclic ring, $R^1$, $R^2$ and $R^3$ conjointly with the adjacent carbon atoms may also be a bicyclic radical, $R^2$, $R^3$ and $R^5$ may also each be hydrogen, $R^4$ may also be hydrogen or halogen and $R^6$ may also be a cycloaliphatic radical, wherein an aromatic carbamic acid ester of the formula

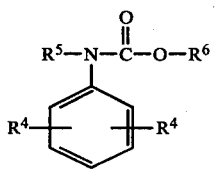

where $R^4$, $R^5$ and $R^6$ have the above meanings, is reacted with an olefin of the formula

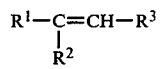

where $R^1$, $R^2$ and $R^3$ have the above meanings, in the presence of an inorganic acid or sulfonic acid.

2. A process as claimed in claim 1, wherein the reaction is carried out with from 0.3 to 5 moles of olefin per mole of carbamic acid ester II.

3. A process as claimed in claim 1, wherein the reaction is carried out at from 25° to 160° C.

4. A process as claimed in claim 1, wherein the reaction is carried out at from 40° to 150° C.

5. A process as claimed in claim 1, wherein the reaction is carried out under a pressure of from 1 to 30 bar.

6. A process as claimed in claim 1, wherein the reaction is carried out with a residence time of from 0.5 to 10 hours.

7. A process as claimed in claim 1, wherein the reaction is carried out with a throughput of from 1 to 120 kilograms of starting material II per kilogram of catalyst per hour.

8. A process as claimed in claim 1, wherein the reaction is carried out with from 0.01 to 0.5 equivalent of acid per mole of starting material II.

9. A process as claimed in claim 1, wherein the reaction is carried out with an organic cation exchanger containing sulfonic acid groups.

10. A process as claimed in claim 1, wherein the reaction is carried out with an organic cation exchanger, containing sulfonic acid groups, which has a particle size of from 5 to 2,000 micrometers.

11. A process as claimed in claim 1, wherein the reaction is carried out with from 1 to 70 percent by weight, based on carbamic acid ester, of an ion exchanger.

12. A process as claimed in claim 1, wherein the reaction is carried out whilst stirring the mixture at not less than 100 rpm.

* * * * *